United States Patent
Hashizume et al.

(10) Patent No.: US 10,271,782 B2
(45) Date of Patent: Apr. 30, 2019

(54) LIQUID COLLECTING APPARATUS AND LIQUID COLLECTING METHOD

(75) Inventors: Nobuya Hashizume, Kyoto (JP);
Keishi Kitamura, Kyoto (JP);
Takahiro Nishimoto, Kyoto (JP);
Yuichi Kimura, Chiba (JP); Hiroshi Toyama, Aichi (JP); Takashi Yamada, Aichi (JP)

(73) Assignees: SHIMADZU CORPORATION, Kyoto (JP); NATIONAL INSTITUTES FOR QUANTUM AND RADIOLOGICAL SCIENCE AND TECHNOLOGY, Chiba (JP); NATIONAL CENTER FOR GERIATRICS AND GERONTOLOGY, Aichi (JP)

( * ) Notice: Subject to any disclaimer, the term of this patent is extended or adjusted under 35 U.S.C. 154(b) by 972 days.

(21) Appl. No.: 14/425,317

(22) PCT Filed: Sep. 3, 2012

(86) PCT No.: PCT/JP2012/005574
§ 371 (c)(1),
(2), (4) Date: Oct. 5, 2015

(87) PCT Pub. No.: WO2014/033798
PCT Pub. Date: Mar. 6, 2014

(65) Prior Publication Data
US 2016/0029934 A1 Feb. 4, 2016

(51) Int. Cl.
*A61B 5/155* (2006.01)
*A61B 5/15* (2006.01)
(Continued)

(52) U.S. Cl.
CPC .......... *A61B 5/155* (2013.01); *A61B 5/15003* (2013.01); *A61B 5/153* (2013.01);
(Continued)

(58) Field of Classification Search
CPC ..................................................... A61B 5/155
See application file for complete search history.

(56) References Cited

U.S. PATENT DOCUMENTS

| | | | |
|---|---|---|---|
| 4,658,655 | A | 4/1987 | Kanno |
| 2001/0031932 | A1 | 10/2001 | Blake et al. |
| 2011/0098597 | A1 | 4/2011 | Wu et al. |

FOREIGN PATENT DOCUMENTS

| | | |
|---|---|---|
| JP | 60-029150 A | 2/1985 |
| JP | 2001-116666 A | 4/2001 |
| JP | 2003-530188 A | 10/2003 |
| JP | 2009-515146 A | 4/2009 |

OTHER PUBLICATIONS

Hsiao Ming Wu et. al., "In Vivo Quantitation of Glucose Metabolism in Mice Using Small-Animal PET and a Microfluidic Device", J Nucl Med, vol. 48, pp. 837-845, 2007.

(Continued)

*Primary Examiner* — Daniel L Cerioni
*Assistant Examiner* — Yasmeen S Warsi
(74) *Attorney, Agent, or Firm* — McDermott Will & Emery LLP

(57) ABSTRACT

A suction drain device of a disclosed liquid collecting apparatus actively pushes and pulls blood. This achieves liquid collection at high speed even under decreased pressure depending on a physiological state of an animal. Moreover, the liquid collecting apparatus includes a first flow path and a second flow path having a given length. Accordingly, the flow path with a given length set in advance and thus a known volume allows collection of a given amount volume of blood without measuring a length and an amount of blood using a volume measuring device. Accordingly, no need of the measuring device allows reduction in size of the liquid collecting apparatus. Consequently, the liquid collecting apparatus can be installed adjacent to (Continued)

the animal to achieve reduction in dead volume. Moreover, blood is flown to a fourth flow path branched with a connecting terminal, and is also flown to the second flow path branched with a connecting terminal. The blood flown in the second flow path is collected at the highest priority. This obtains collection of fresh blood from a collecting source as a blood supply source.

10 Claims, 9 Drawing Sheets

(51) Int. Cl.
    *A61B 5/153*     (2006.01)
    *A61B 5/157*     (2006.01)
(52) U.S. Cl.
    CPC ........ *A61B 5/157* (2013.01); *A61B 5/150221* (2013.01); *A61B 5/150229* (2013.01); *A61B 5/150236* (2013.01); *A61B 5/150244* (2013.01); *A61B 5/150992* (2013.01); *A61B 2503/40* (2013.01)

(56) References Cited

OTHER PUBLICATIONS

L. Convert et al., "A Microvolumetric beta Blood Counter for Pharmacokinetic PET Studies in Small Animals", IEEE Nuclear Science, vol. 54, No. 1, Feb. 2007, pp. 1-8.
"Blood Sampler twilite", [online], Swisstrace, Internet URL: http://www.swisstrace.ch/blood-sampler-twilite.html, downloaded on Aug. 14, 2012.
International Search Report issued in International Application No. PCT/JP2012/005574 dated Oct. 9, 2012, with English Translation.

LIQUID COLLECTING APPARATUS AND LIQUID COLLECTING METHOD

RELATED APPLICATIONS

This application is a national phase of International Application No. PCT/JP2012/005574, filed on Sep. 3, 2012, the disclosure of which Application is incorporated by reference herein.

TECHNICAL FIELD

The present invention relates to a liquid collecting apparatus and a liquid collecting method of collecting a target liquid to be collected as separated in a time series.

BACKGROUND ART

The following describes a liquid collecting apparatus taking a blood collecting apparatus that collects blood as one example. The blood collecting apparatus is used for quantitative analyses in nuclear medicine diagnosis (e.g., PET (Positron Emission Tomography)) and so on. In the nuclear medicine diagnosis, the quantitative analyses of information on a vital function, such as concentrations of nerve receptors and metabolism of tumor, require measurement of a time variation in agent concentration of plasma in arterial blood, i.e., a radioactive concentration. The following modes are adopted in an automatic blood collecting apparatus for measuring a radioactive concentration in blood. See, for example, Patent Literatures 1 and 2, and Non-Patent Literatures 1 to 3. The apparatus are used for measuring a radioactive concentration in arterial blood of small animals (e.g., mice, rats and so on). It should be noted that the automatic blood collecting apparatus in Patent Literature 2 differs from those in the other modes in purpose of use.

[Patent Literature 1, Non-Patent Literature 1] Disclosed is a mode of introducing arterial blood flown out due to pressure of blood of a mouse itself onto a microchip (microelement) MC as illustrated in FIG. 9. The microchip MC has one main flow path $F_M$, selectable branch flow paths $F_B$, and a side flow path $F_N$ arranged therein. The side flow path $F_N$ flows a heparin solution H used for cleaning the flow paths and ejecting blood B or flowing out the heparin solution H and the blood B. The branch flow paths $F_B$ each include a container, and one of the flow paths is selectable depending on pressure of an argon gas G as supplied to the microchip MC and a mechanism of the microchip MC. The blood B is flown under a state where one of the branch flow paths $F_B$ is selected. Each of the flow paths $F_M$ and $F_B$ is grooved by a given size relative to the microchip MC. A length or an area of the groove into which the blood B is flown allows specification of a minute volume of the blood B. This is a characteristic of the microchip MC. With the specified minute volume, the heparin solution H is pushed under the state where the flow path is filled with a given volume of blood B, whereby the blood B is flown to a given receiver (not shown). Thereafter, each of the flow paths $F_M$ and $F_B$ is cleaned with the heparin solution H. Then the process is prepared for next blood collection. The blood B in the receiver is sucked up with physiological saline into another container, and radiation in the blood B is counted using a well counter.

[Non-Patent Literature 2] In Non-Patent Literature 2, a radiation detector is installed to sandwich a part of a catheter inserted into arteria to measure a radioactive concentration in blood. An elongated diode has a length of 30 [mm] A tube containing blood is arranged along a long side of the diode, causing an increased detectable area. This achieves ensured detection efficiency of β+-rays. The catheter includes one end connected to a syringe pump. The catheter pulls the syringe pump at a certain rate to draw blood. A flow rate of blood is calculated from the rate and a volume of blood is calculated from an internal diameter of the catheter, whereby a radioactive concentration is measured.

[Non-Patent Literature 3] As illustrated FIG. 10 in Non-Patent Literature 3, blood is returned into the vein V from the end of catheter C inserted into the arteria A. A LYSO detector D and a Perista pump P are installed in a part of the catheter C. $β^+$-rays in the arterial blood flowing inside the interior catheter C are annihilated to generate γ-rays. The γ-rays enter into the LYSO detector D to emit light, and the number of optical fibers F is counted with the light in a collecting box B. The Perista pump P controls a flow rate of blood. A control PC calculates a volume of blood from the flow rate and the internal diameter of the catheter, thereby measuring a radioactive concentration.

[Patent Literature 2] A flow path is switched by a five-way joint to repeat ejection of blood or a cleaning liquid and collection of blood.

Patent Literature 1: Japanese Patent Publication (Translation of PCT Application) 2009-515146A Patent Literature 2: Japanese Patent Publication No. 2001-116666A Non-Patent Literature 1: H.-M. Wu, G Sui, C.-C. Lee, M. L. Prins, W. Ladno, H.-D. Lin, A. S. Yu, M. E. Phelps, and S.-C. Huang, "In vivo quantitation of glucose metabolism in mice using small-animal PET and a microfluidic device", J Nucl Med, vol. 48, pp. 837-845, 2007.

Non-Patent Literature 2: L. Convert, G M. Brassard, J. Cadorette, D. Rouleau, E. Croteau, M. Archambault, R. Fontaine, and R. Lecomte, "A microvolumetric β blood counter for pharmacokinetic PET studies in small animals," IEEE Nuclear Sci, vol. 54, no. 1, 2007.

Non-Patent Literature 3: Non-Patent Literature 2: "Blood Sampler twilite", [online], Swisstrace, Internet URL: http://www.swisstrace.ch/blood-sampler-twilite.html

SUMMARY OF INVENTION

Technical Problem

However, the above modes possess the following problems. Especially, for Patent Literature 2 mentioned above, the blood should be pushed back into animals. Such a process is performed for every completion of blood collection in order to achieve reduction in blood loss. However, when the blood is directly collected from the animals, the pushed back blood is not flown to the periphery of arteria but remains around a portion where blood collection is performed. As a result, no fresh blood is collected. Such a problem may arise.

The present invention has been made regarding the state of the art noted above, and its object is to provide a liquid collecting apparatus and a liquid collecting method that allow collection of a fresh liquid.

Solution to Problem

To fulfill the above object, Inventors have made intensive research and attained the following findings.

Specifically, a conventional idea to push back the collect blood to an original animal for reduction in blood loss was changed, and attention has been focused on continuous flow of blood from a collecting source side as a liquid supply side. Accordingly, the following finding has been attained. That is, it is effective to flow blood from a collecting source side into a branched flow path and also to another branched flow path away from the collecting source side, thereby collecting the blood flowing in the other branched flow path away from the collecting source side at the highest priority.

The present invention based on the above finding adopts the following configuration. One embodiment of the present invention discloses a liquid collecting apparatus collecting a target liquid to be collected as separated in a time series. The liquid collecting apparatus includes a flow path having a given length, a suction drain device connected to the flow path and pushing and pulling the target liquid to be collected, a first connecting terminal branching the flow path into a plurality of flow paths toward the suction drain device, a first opening and closing device opening and closing the flow paths on a side adjacent to the suction drain device, a second connecting terminal branching the flow path into a plurality of flow paths toward a collecting source, a second opening and closing device opening and closing the flow paths branched with the second connecting terminal, and a dropping port connected to each of the flow paths branched with the first connecting terminal and dropping the liquid to be collected as separated. The flow path is a tube. The first opening and closing device is a pinch valve that closes the flow path formed by the tube by application of external pressure and opens the flow path formed by the tube by releasing the external pressure. The pinch valve constituting the first opening and closing device opens one of two flow paths formed by the tube while closing the other.

With the liquid collecting apparatus according to the present embodiment, the suction drain device actively pushes and pulls the target liquid to be collected. This achieves liquid collection regardless of a supply source (collection source) of the liquid. For instance, when the target liquid to be collected is blood of an animal, blood collection is performable even under decreased blood pressure depending on a physiological state of the animal. As a result, liquid collection is obtainable even with decreased blood pressure of the animal. Moreover, the liquid collecting apparatus includes the flow path having a given length. Accordingly, the flow path with a given length set in advance and thus a known volume allow collection of a given volume of liquid without measuring a length and an amount of the target liquid to be collected using a volume measuring device (e.g., optical measuring device). In this manner, no need of the measuring device achieves reduction in size of the liquid collecting apparatus. Consequently, the liquid collecting apparatus can be installed close to a collecting source (e.g., an animal) of the liquid. This achieves elimination of a factor responsible for a distortion of a concentration waveform, such as reduction, delay, or dispersion of a dead volume (indicating a void volume). Moreover, the liquid collecting apparatus further includes the first and second connecting terminals as well as the first and second opening and closing devices. The second opening and closing device flows the target liquid to be collected from the side adjacent to the collecting source as the liquid supply side to the flow path branched with the second connecting terminal, and the first opening and closing device flows the target liquid to be collected into another flow path branched with the first connecting terminal away from the side adjacent to the collecting source. This allows the second opening and closing device to flow the target liquid to be collected continuously. Consequently, the fresh liquid continuously can flow without pushing the target liquid to be collected flowing away from the side adjacent to the collecting source back into the side adjacent to the collecting source (i.e., the upstream), and thus the target liquid to be collected can flow into the flow path branched with the first connecting terminal away from the side adjacent to the collecting source as necessary (in a collecting time) and can be collected. This allows collection of a fresh liquid from the collecting source as a liquid supply source.

The flow path mentioned above is a tube. A tube has a restoring force against external pressure. Accordingly, the first opening and closing device or the second opening and closing device can be formed by a pinch valve to be mentioned later. In addition, the first opening and closing device is the pinch valve that closes the flow path formed by the tube by application of external pressure and opens the flow path formed by the tube by releasing the external pressure. The flow path in the present embodiments has a dead volume smaller than that of a valve (opening and closing device) into which a liquid is inserted. Moreover, only replacement of the flow path formed by the tube is required. Accordingly, no replacement of the first opening and closing device is required. Furthermore, the opening and closing device formed by the pinch valve is small in size. Consequently, the device can be installed adjacent to the liquid supply source (collecting source). Moreover, a factor responsible for a distortion of a concentration waveform, such as reduction, delay, or dispersion of a dead volume (indicating a void volume) can be eliminated. For instance, when the target liquid to be collected is blood of an animal, the pinch valve can be installed adjacent to the animal as the collecting source. In addition, the tube may be formed to have a small diameter (to be thin). Consequently, since the flow path in which the liquid flows becomes thinner, opening and closing of the tube with the pinch valve using the thin tube as the flow path achieves reduction in volume of the flow path and in volume of the liquid to flow.

Moreover, a suppressed flow rate is obtainable by reduction in volume of the flow path and in volume of the liquid to flow. For instance, when the target liquid to be collected is blood, minimalized reduction in blood loss due to continuous flow of the blood is obtainable.

The pinch valve constituting the first opening and closing device opens one of two flow paths formed by the tube while closing the other. With the construction that the pinch valve opens one flow path while closing the other, one pinch valve allows opening and closing of the two flow paths. This achieves reduction in number of components of the first opening and closing device.

Similar to the first opening and closing device, examples of the second opening and closing device include a pinch valve. As is described in Operation and Effect of the first opening and closing device, only replacement of the flow path formed by a tube is required. Accordingly, replacement of the second opening and closing device is not required. The pinch valve can be installed adjacent to the liquid supply source (collecting source). This achieves further reduction in dead volume between the collecting source and the opening and closing device.

Blood has been described as one example of the target liquid to be collected in the liquid collecting apparatus of the present embodiment. In this case, the liquid collecting apparatus is an apparatus that collects the blood (i.e., a blood collecting apparatus). It should be noted that the liquid is not limited to blood as long as it corresponds to the target liquid to be collected. For instance, physiological fluid other than blood (e.g., lymph, a protein-containing liquid, and so on), a fluorescence agent-containing liquid, and a mixed liquid used for an analyzer may be used.

Another embodiment of the present invention discloses a liquid collecting method of collecting a target liquid to be collected as separated in a time series using a liquid collecting apparatus. The liquid collecting apparatus is provided with a flow path having a given length, a suction drain device connected to the flow path and pushing and pulling the target liquid to be collected, a first connecting terminal branching the flow path into a plurality of paths toward the suction drain device, a first opening and closing device opening and closing the flow paths on a side adjacent to the suction drain device, a second connecting terminal branching the flow path into a plurality of paths toward a side adjacent to a collecting source, a second opening and closing device opening and closing the flow paths branched with the second connecting terminal, and a dropping port connected to each of the flow paths branched with the first connecting terminal and dropping the liquid to be collected as separated. The method includes filling a part of the flow path adjacent to the suction drain device rather than the target liquid to be collected with a fluid composed of at least either a liquid or a gas, pushing and pulling the fluid, with which the part of the flow path adjacent to the suction drain device is filled, through control of the suction drain device, the first opening and closing device, and the second opening and closing device, thereby controlling movement of the target liquid to be collected, and flowing the target liquid to be collected to the flow path branched with the second connecting terminal and flowing the target liquid to be collected to the flow path branched with the first connecting terminal, thereby collecting the liquid flowing in the flow path branched with the first connecting terminal at the highest priority.

With the liquid collecting method according to the present embodiment, the liquid is collected using the liquid collecting apparatus according to the embodiment. This allows collection of the liquid by a given volume without measuring a length or an amount of the target liquid to be collected with a volume measuring device (e.g., an optical measuring device). Moreover, the target liquid to be collected flows into the flow path branched with the second connecting terminal and into the flow path branched with the first connecting terminal, and the liquid flowing in the flow path branched with the first connecting terminal is collected at the highest priority. This achieves collection of a fresh liquid from the collecting source as a liquid supply source.

The liquid collecting method according to the present embodiment preferably performs collection as under. That is, the fluid with which a part of the flow path adjacent to the suction drain device is filled is sucked toward the suction drain device, whereby the target liquid to be collected is sucked. The fluid with which the part of the flow path adjacent to the suction drain device is filled is pushed back into the collecting source, whereby the target liquid to be collected is pushed back. The first opening and closing device is so configured as to open and close a first flow path as the flow path that is located upstream of the first connecting terminal, and as to open and close a second flow path as the flow path that is located downstream of the first connecting terminal and upstream of the dropping port. The suction drain device is so configured as to connect to a third flow path of a plurality of flow paths branched with the first connecting terminal, the third flow path being as another flow path different from the second flow path connected to the dropping port. The second opening and closing device is so configured as to open and close a fourth flow path as the flow path located downstream of the second connecting terminal branched from the first flow path with the second connecting terminal. The liquid collecting method preferably includes a first drain step, a first suction step, a second drain step, and a second suction and third drain step. In the first drain step, the first opening and closing device opens the first flow path and closes the second flow path. The second opening and closing device opens the fourth flow path. Under such a condition, the suction drain device pushes and pulls the fluid until an upstream end of the fluid reaches the second connecting terminal, thereby flowing the target liquid to be collected to the fourth flow path. In the first suction step after the first drain step, the first opening and closing device opens the first flow path and closes the second flow path. The second opening and closing device closes the fourth flow path. Under such a condition, the suction drain device sucks the fluid until a boundary between the upstream end of the fluid and the target liquid to be collected is located adjacent to the suction drain device rather than the first connecting terminal, thereby sucking the liquid. In the second drain step after the first suction step, the first opening and closing device closes the first flow path, and opens the second flow path. The second opening and closing device opens the flow path. Under such a condition, the suction drain device pushes the fluid back together with the target liquid to be collected sucked in the first suction step. Then the fluid is stopped at the dropping port via the second flow path, and the target liquid to be collected is ejected and collected from the dropping port while the liquid adjacent to the collecting source is flown to the fourth flow path. In the second suction and the third drain step after the second drain step, the first opening and closing device closes the first flow path and opens the second flow path. The second opening and closing device opens the fourth flow path. Under such a condition, the suction drain device sucks the fluid until the upstream end of the fluid is located adjacent to the suction drain device rather than the first connecting terminal, thereby flowing the liquid adjacent to the collecting source to the fourth flow path while the target liquid to be collected is sucked.

With the liquid collecting method including the above steps, the first drain step, the first suction step, the second drain step, and the second suction and third drain step are performed in turn. Consequently, the target liquid to be collected is drained to the fourth flow path branched with the second connecting terminal, and is drained to the second flow path branched with the first connecting terminal. Then the liquid flowing in the second flow path branched with the first connecting terminal is collected at the highest priority. This achieves efficient collection of a fresh liquid.

Moreover, the method further includes a pushing back step after the second suction and third drain step. In the pushing back step, the first opening and closing device opens the first flow path and closes the second flow path. The second opening and closing device opens the fourth flow path. Under such a condition, the fluid is pushed together with the target liquid to be collected sucked in the second suction and third drain step until the upstream end of the fluid is located to the second connecting terminal, whereby the liquid adjacent to the collecting source is flown to the fourth flow path. After the pushing back step, the first suction step, the second drain step, and the second suction and third drain step are repeatedly performed. Such is preferable. This achieves multiple-time collection of a fresh liquid with high efficiency.

Examples of the fluid include both liquid and gas as under, a gas only, and a liquid only. That is, for the fluid composed of a liquid and a gas as the first example, the part of the flow path adjacent to the suction drain device is filled with the liquid. The gas is inserted into the flow path between the liquid with which the part of the flow path adjacent to the suction drain device is filled and the target liquid to be collected. The suction drain device pushes and pulls the liquid with which the part of the flow path adjacent to the suction drain device is filled, thereby controlling movement of the target liquid to be collected. As noted above, filling the flow path with the liquid different from the target liquid to be collected and inserting the gas between the liquid and the target liquid to be collected allows reduction in volume of gas compressed or expanded due to push and pull by the suction drain device. This achieves movement of the target liquid to be collected with high accuracy. Moreover, the gas is inserted between the liquid with which the flow path adjacent to the suction drain device is filled and the target liquid to be collected. This allows prevention of mixing due to contact of the former liquid and the latter liquid (target to be collected). This also allows prevention of dilution of the target liquid to be collected resulting from the mixing.

Moreover, for the fluid composed of a gas as another example, the part of the flow path adjacent to the suction drain device rather than the target liquid to be collected is filled with the gas. The suction drain device pushes and pulls the gas with which the part of the flow path adjacent to the suction drain device is filled, thereby controlling movement of the target liquid to be collected. With the example, the suction drain device pushes and pulls the gas for a medium. This allows control of the movement of the target liquid to be collected.

For the fluid composed of a liquid as the last example, the part of the flow path adjacent to the suction drain device rather than the target liquid to be collected is filled with the liquid. The suction drain device pushes and pulls the liquid with which the part of the flow path adjacent to the suction drain device is filled, thereby controlling movement of the target liquid to be collected. With the example, the suction drain device pushes and pulls the liquid for a medium. This allows control of the movement of the target liquid to be collected.

As mentioned above, blood has been described as one example of the target liquid to be collected in the liquid collecting method of the present embodiment. In this case, the liquid collecting method corresponds to a method of performing blood collection (i.e., a blood collecting method). As described in the blood collecting apparatus, the liquid is not limited to blood as long as it corresponds to the target liquid to be collected. For instance, physiological fluid other than blood (e.g., lymph, a protein-containing liquid, and so on), a fluorescence agent-containing liquid, and a mixed liquid used for an analyzer may be used.

Advantageous Effects of Invention

With the liquid collecting apparatus and the liquid collecting method according to the present invention, the target liquid to be collected flows into the flow path branched with the second connecting terminal and flows into the flow path branched with the first connecting terminal, and the liquid flowing in the flow path branched with the first connecting terminal is collected at the highest priority. This achieves collection of a fresh liquid from the collecting source as a liquid supply source. In the liquid collecting apparatus according to the present embodiments, the flow path is a tube. A tube has a restoring force against external pressure. Accordingly, the first opening and closing device or the second opening and closing device can be formed by a pinch valve. Moreover, the first opening and closing device is the pinch valve that closes the flow path formed by the tube by application of external pressure and opens the flow path formed by the tube by releasing the external pressure. Accordingly, no replacement of the first opening and closing device is required, leading to elimination of a factor responsible for a distortion of a concentration waveform, such as reduction, delay, or dispersion of a dead volume (indicating a void volume). The construction of the pinch valve to open one path while closing the other path achieves opening and closing of the two flow paths with one pinch valve. This allows reduction in number of components of the first opening and closing device.

EMBODIMENT 1

Figure 1:
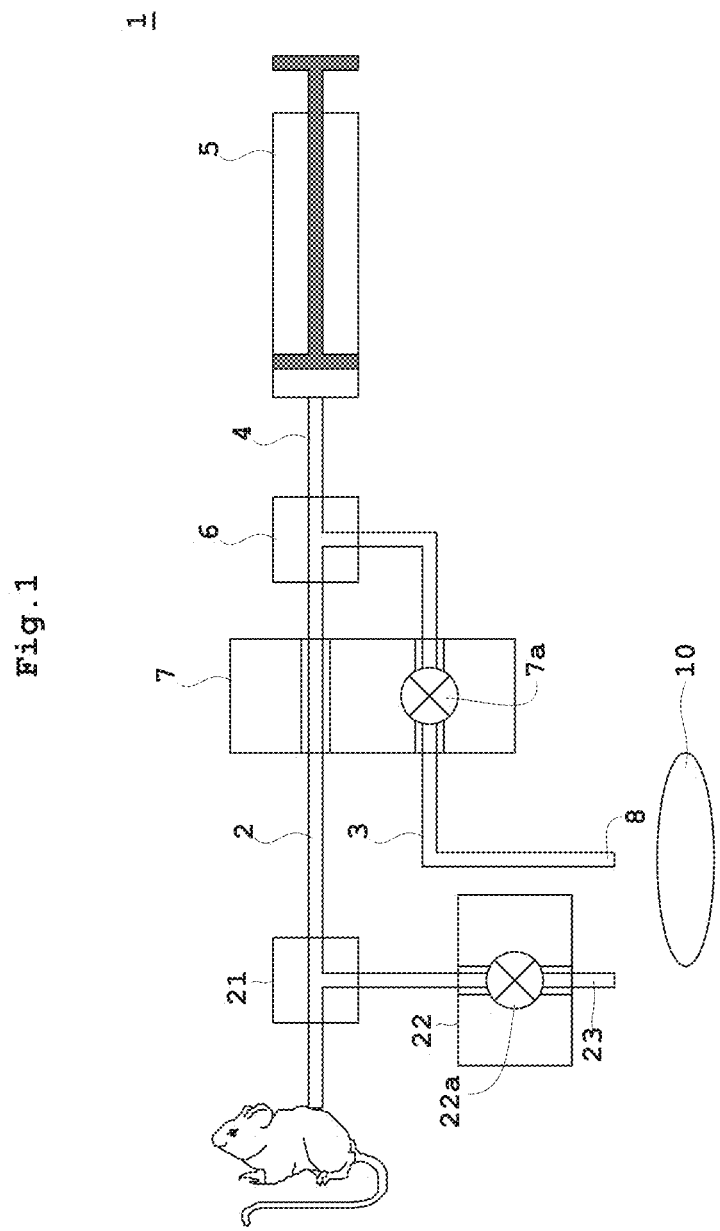
FIG. 1 schematically illustrates a blood collecting apparatus according to each of embodiments of the present invention.

The following describes Embodiment 1 with reference to drawings. FIG. 1 schematically illustrates a blood collecting apparatus according to one embodiment of the present invention. Embodiment 1 as well as Embodiments 2 and 3 to be mentioned later describe blood as one example of a target liquid to be collected and a blood collecting apparatus as one example of a liquid collecting apparatus.

As illustrated in FIG. 1, a blood collecting apparatus 1 according to each embodiment of the present invention collects target blood to be collected as separated in a time series. Around the blood collecting apparatus 1, a container 10 is provided for storing collected blood. The Embodiment 1 as well as Embodiments 2 and 3 to be mentioned later measure a radioactive concentration in arterial blood of small animals (e.g., mice and rats). Moreover, a centrifuge (not shown) spins the container 10 for performing centrifugal separation. In each of the embodiments, the centrifugal separation is performed to blood. Accordingly a plasma separation is performed, and radiation contained in plasma and blood cell resulting from the plasma separation is measured. The blood collecting apparatus 1 corresponds to the liquid collecting apparatus in the present invention.

The blood collecting apparatus 1 includes a flow path (a first flow path 2, a second flow path 3, a third flow path 4, and a fourth flow path 23 in the embodiments) having a given length, a suction drain mechanism 5 connected to the third flow path 4 of the flow path for pushing and pulling target blood to be collected, a connecting terminal 6 branching the flow path into a plurality of paths (two paths in each of the embodiments), a pinch valve 7 opening and closing the flow path (the first flow path 2 and the second flow path 3 in each of the embodiments), and a dropping port 8 connected to the branched flow path (the second flow path 3 in each of the embodiments) for dropping the separated target blood to be collected. The first flow path 2, the second flow path 3, the third flow path 4, and the fourth flow path 23 correspond to the flow path in the present invention. The first flow path 2 corresponds to the first flow path in the present invention. The second flow path 3 corresponds to the second flow path in the present invention. The third flow path 4 corresponds to the third flow path in the present invention. The fourth flow path 23 corresponds to the fourth flow path in the present invention. The suction drain mechanism 5 corresponds to the suction drain device in the present invention. The connecting terminal 6 corresponds to the first opening and closing device in the present invention. The pinch valve 7 corresponds to the first opening and closing device as well as the pinch valve in the present invention. The dropping port 8 corresponds to the dropping port 8 in the present invention.

Except for the case of pushing back blood, a side adjacent to the collecting source (small animals in the present embodiment) corresponds to upstream, and a side adjacent to the dropping port 8 corresponds to downstream, taking a flow of blood upon collection as a reference. Accordingly, in the specification, a flow path located upstream of the connecting terminal 6 is the first flow path 2, and a flow path located downstream of the connecting terminal 6 and upstream of the dropping port 8 is the second flow path 3. The suction drain mechanism 5 is so configured as to be connected to the third flow path 4 as another flow path different from the second flow path 3 connected to the dropping port 8.

A tube having a small sectional area (i.e., a small diameter) is adopted for the flow path (the first flow path 2, the second flow path 3, the third flow path 4, and the fourth flow path 23) for reduction in amount of blood to be collected. In each of the present embodiments, two types of tubes are used. That is, a polyethylene tube having an internal diameter of 0.28 [mm] and a tube (SILASCON tube) having only a portion pinched by the pinch valve 7 or a pinch valve 22 opening and closing the fourth flow path 23 to be mentioned later made from SILASCON (Registered Trademark) as one type of silicone are used. The portion has an internal diameter of 0.5 [mm] and is softer than the polyethylene tube and thus has a restoring force. The first flow path 2 and the second flow path 3 of the flow path each have a predetermined length for achieving control of movement of a liquid (blood in each of the present embodiments) by merely push and pull with the suction drain mechanism 5. Of course, the third flow path 4 connected to the suction drain mechanism 5 may have a predetermined length.

A syringe pump is used as the suction drain mechanism 5. Usage of the syringe pump as the suction drain mechanism 5 achieves collection of the liquid (blood) by pushing and pulling the liquid (blood in each of the present embodiments) of several [μL] at a high rate and high accuracy. In addition, even if blood pressure varies depending on a physiological state of animals, stable blood collection is obtainable with no influence of the variation. As noted above, the suction drain mechanism 5 is a syringe pump that allows accurate push and pull of the liquid (blood). The first flow path 2 and second flow path 3 each having a predetermined length and a predetermined sectional area allows calculation of a volume. Consequently, blood flowing in the first flow path 2 or the second flow path 3 can be moved by a volume pushed and pulled by the suction drain mechanism 5.

Moreover, a liquid and a gas is used as the medium (fluid) to be pushed and pulled. Moreover, the gas to be pushed and pulled may be air. Alternatively, the gas may be an inert gas representative of a noble gas such as helium, neon, and argon, or a nitrogen gas that does not react with blood or a heparin solution. Moreover, the liquid to be pushed and pulled is not particularly limited. A cleaning liquid is preferably used as the liquid that is representative of a heparin solution used for cleaning a flow path or ejecting blood. In addition, a liquid with low viscosity, such as water or a mineral oil, is preferable for enhancing accuracy in control of the blood.

The connecting terminal 6 connects the first flow path 2, the second flow path 3, and the third flow path 4. In each of the present embodiments, the connecting terminal 6 uses a block made of a PDMS (polydimethylsiloxane) resin and having minute holes for the flow path. The holes are connected to the first flow path 2, the second flow path 3, and the third flow path 4 individually. Taking the upstream as a reference, the connecting terminal 6 branches the first flow path 2 into two paths, i.e., the second flow path 3 and the third flow path 4.

In each of the present embodiments, the pinch valve 7 is used as the first opening and closing device for opening and closing the flow path. The pinch valve 7 is so configured as to close the flow path (the first flow path 2 and the second flow path 3) formed by the tube through application of pressure from outside the tube (see a "blocking part 7a" in FIG. 1 and FIG. 3 mentioned later). The pinch valve 7 is also so configured as to open the flow path (first flow path 2 and second flow path 3) formed by the tube through release of the pressure from outside the tube. Moreover, in each of the present embodiments, the pinch valve 7 is so configured as to close one of the two flow paths (the first flow path 2 and the second flow path 3) formed by the tube when opening the other of the flow paths. Consequently, the pinch valve 7 switches the blocking part 7a so as to close the second flow path 3 when opening the first flow path 2, and conversely so as to close the first flow path 2 when opening the second flow path 3.

A new branched portion and an opening and closing device (second opening and closing device) are additionally provided. As illustrated in FIG. 1, provided are a connecting terminal 21 branching the flow path into a plurality of paths (two paths in each of the embodiments), and the pinch valve 22 opening and closing the flow path (the fourth flow path 23 in each of the embodiments) branched with the connecting terminal 21. The flow path branched from the first flow path 2 with the connecting terminal 21 and located downstream of the connecting terminal 21 is the fourth flow path 23. The connecting terminal 21 corresponds to the second connecting terminal in the present invention. The pinch valve 22 corresponds to the second opening and closing device in the present invention.

The connecting terminal 6 corresponding to the first connecting terminal branches the first flow path 2 into two flow paths, i.e., the second flow path 3 and the third flow path 4. The pinch valve 7 corresponding to the first opening and closing device closes the flow path (the first flow path 2 and the second flow path 3 in each of the embodiments) on a side adjacent to the suction drain mechanism 5. In addition, the connecting terminal 21 corresponding to the second connecting terminal branches the first flow path 2 into two flow paths. Here, one of the branched flow paths other than the flow path 2 connected to the suction drain mechanism 5 (the third flow path 4 on the downstream) is the fourth flow path 23. The pinch valve 22 corresponding to the second opening and closing device opens and closes the fourth flow path 23 branched with the connecting terminal 21.

Similar to the pinch valve 7 corresponding to the first opening and closing device in the present invention, the pinch valve 22 is used as the second opening and closing device for pinching a tube. The pinch valve 22 differs from the pinch valve 7 in the feature to open and close one flow path (the fourth flow path 23) formed by a tube. The blocking part 22a illustrated in FIG. 1 and FIG. 3 to be mentioned later is a portion to which pressure is applied via the pinch valve 22 from outside the tube (i.e., a portion to be pinched).

Figure 2:
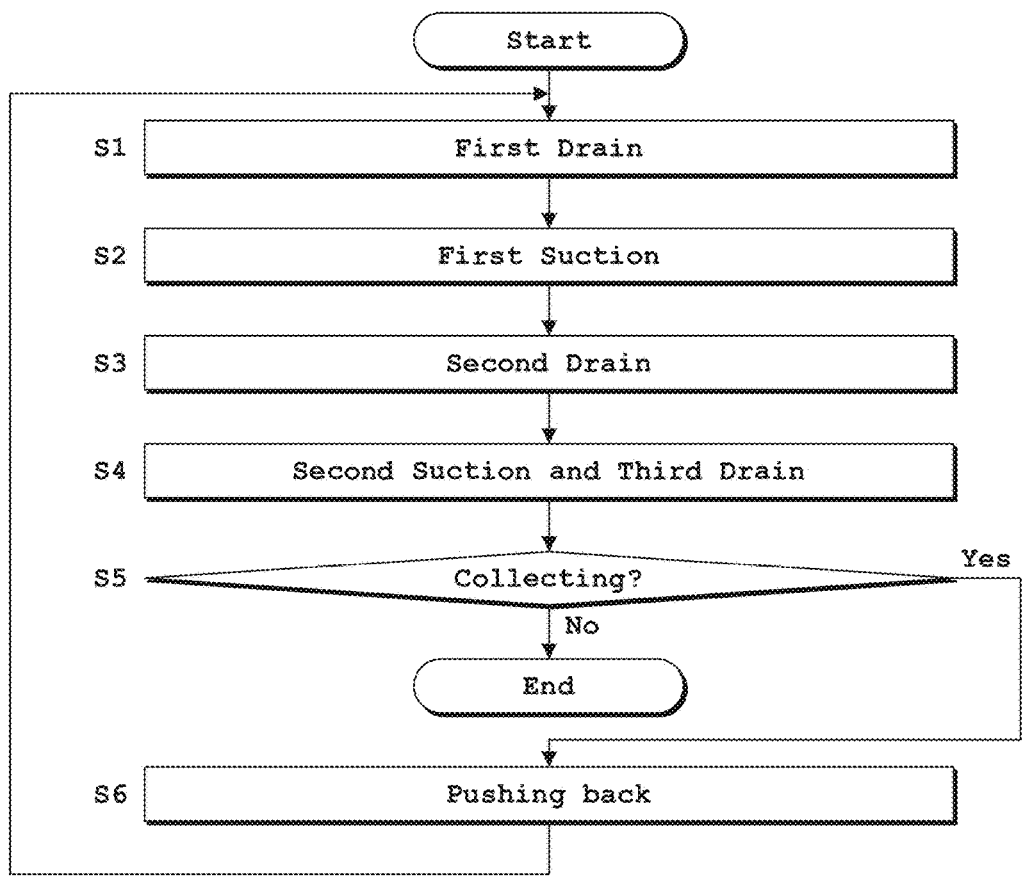
FIG. 2 is a flow chart of a series of blood collecting processes according to each of the embodiments.
Figure 3:
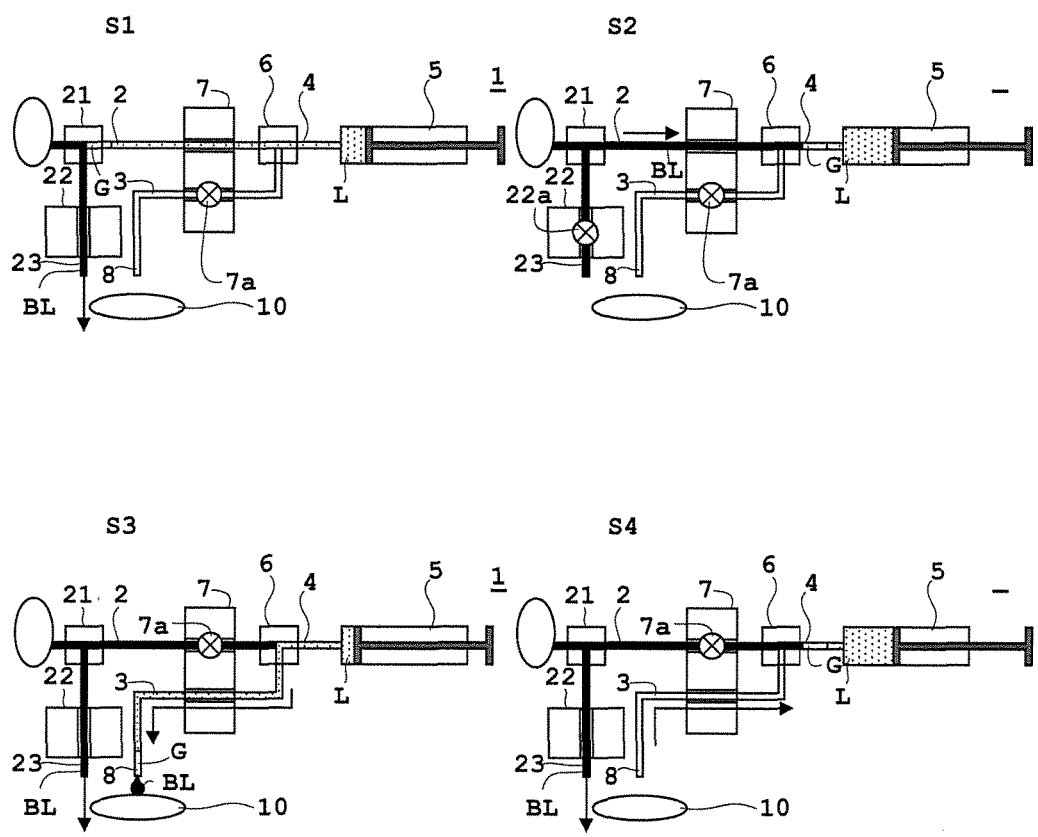
FIG. 3 schematically illustrates a series of blood collecting processes in turn according to Embodiment 1.

The following describes a series of blood collection processes with reference to FIGS. 2 and 3. FIG. 2 is a flow chart of a series of blood collecting processes according to each of the present embodiments. FIG. 3 schematically illustrates the series of blood collecting processes in turn according to Embodiment 1. Here in FIG. 3, the numeral BL denotes the target blood to be collected, the numeral L denotes a liquid different from the target blood BL, and the numeral G denotes a gas. Moreover, in FIG. 3, the target blood BL is indicated in black, the liquid L is indicated by dotted hatching, and the gas G is indicated in white.

(Step S1) First Drain

A Step S1 in FIG. 3 indicates a standby state prior to blood collection. The pinch valve 7 opens the first flow path 2 and closes the second flow path 3. The pinch valve 22 opens the fourth flow path 23. Under such a condition, the suction drain mechanism 5 pushes and pulls the fluid (the liquid L and the gas G) until an upstream end of the fluid (the liquid L and the gas G in the present embodiment 1) reaches the connecting terminal 21, thereby flowing the blood BL into the fourth flow path 23. Consequently, the first flow path 2 and the third flow path 4 from the connecting terminal 21 to the suction drain mechanism 5 is filled with the fluid (the liquid L and the gas G). This causes the blood BL drawn from the animal to flow continuously into the fourth flow path 23 in an open state. The Step S1 corresponds to the first drain step in the present invention.

(Step S2) First Suction

After the first drain of the Step S1, the pinch valve 7 opens the first flow path 2 and closes the second flow path 3. The pinch valve 22 closes the fourth flow path 23. Under such a condition, the suction drain mechanism 5 sucks the fluid (the liquid L and the gas G) until a boundary between the upstream end of the fluid (the liquid L and the gas G) and the blood BL reaches the side adjacent to the suction drain mechanism 5 rather than the connecting terminal 6, thereby sucking the blood BL. Consequently, the fourth flow path 23 is brought into a closed state. The blood BL drawn from the animal is sucked in an arrow direction to the side adjacent to the suction drain mechanism 5 (the right of FIG. 3) rather than the bifurcation portion at the connecting terminal 6. The Step S2 corresponds to the first suction step in the present invention.

(Step S3) Second Drain

After the first suction in the Step S2, the pinch valve 7 closes the first flow path 2 and opens the second flow path 3 (i.e., switches the blocking part 7a from the second flow path 3 to the first flow path 2). The pinch valve 22 opens the fourth flow path 23. Under such a condition, the blood BL drawn in the Step S1 is pushed back together with the fluid (the liquid L and the gas G). Then the fluid (the liquid L and the gas G) is flown in the second flow path 3 and is stopped with the dropping port 8. The blood BL is ejected and collected from the dropping port 8 while the liquid BL adjacent to the collecting source is flown into the fourth flow path 23. Consequently, the dropping port 8 drops the blood BL through the second flow path 3 into the container 10 in the arrow direction. At this time, the blood BL drawn from the animal is flown into the fourth flow path 23 in the open state. The Step S3 corresponds to the second drain step in the present invention.

(Step S4) Second Suction and Third Drain

After the second drain in the Step S3, the pinch valve 7 closes the first flow path 2 and opens the second flow path 3. The pinch valve 22 opens the fourth flow path 23. Under such a condition, the suction drain mechanism 5 sucks the fluid (the liquid L and the gas G) until the upstream end of the fluid (the liquid L and the gas G) reaches adjacent to the suction drain device 5 rather than the connecting terminal. Consequently, the blood BL adjacent to the collecting source is flown into the fourth flow path 23 while being sucked. Accordingly, the fluid (the liquid L and the gas G) stopped at the dropping port 8 is drained in the arrow direction through the second flow path 3 to a portion adjacent to the suction drain mechanism 5 rather than the bifurcation portion at the connecting terminal 6 (the right in FIG. 3). On the other hand, the blood BL drawn from the animal is flown continuously to the fourth flow path 23 in the open state following the Step S3. The Step S4 corresponds to the second suction and third drain step in the present invention.

(Step S5) Collecting?

Subsequently, if blood collection is performed, the process returns to the process after a Step S6 of pushing back, and the processes in Step S2 to S5 are similarly repeated. If no blood collection is performed, a series of blood collection processes is completed.

(Step S6) Pushing Back

After the second suction and third drain of the Step S4, the pinch valve 7 opens the first flow path 2, and closes the second flow path 3 (i.e., the blocking part 7a is switched from the first flow path 2 to the second flow path 3). The pinch valve 22 opens the fourth flow path 23. Under such a condition, the fluid (the liquid L and the gas G) is pushed together with the blood BL sucked in the Step S4 until the upstream end of the fluid (the liquid L and the gas G) reaches the connecting terminal 21, whereby the blood BL adjacent to the collecting source is flown into the fourth flow path 23. The process returns to the Step S1. As noted above, after the pushing back in the Step S6, the first suction in the Step S2, the second drain in the Step S3, and the second suction and third drain in the Step S4 are repeatedly performed. The Step S6 corresponds to the pushing back step in the present invention.

With the liquid collecting apparatus of Embodiment 1, the suction drain mechanism 5 actively pushes and pulls the target liquid to be collected (blood in the present embodiments), achieving collection of the liquid (blood) regardless of the condition of the supply source (collecting source) of the liquid (blood). As in each of the present embodiments, when the target liquid to be collected is blood of animals, blood collection is performable under decreased blood pressure due to a physiological state of animals. As a result, liquid (blood) collection is obtainable with decreased blood pressure of animals. Moreover, the liquid collecting apparatus 1 includes the flow path (the first flow path 2, the second flow path 3, the third flow path 4, and the fourth flow path 23 in each of the present embodiments) having a given length. Accordingly, the flow path with a given length set in advance and thus a known volume allows collection of a given amount volume of liquid without measuring a length and an amount of the target liquid to be collected (blood) using a volume measuring device (e.g., optical measuring device). In this manner, no need of the measuring device allows reduction in size of the liquid collecting apparatus (the blood collecting apparatus 1 in each of the present embodiments). Consequently, the liquid collecting apparatus can be installed adjacent to a collecting source (e.g., animal) of the liquid. This achieves elimination of a factor responsible for a distortion of a concentration waveform, such as reduction, delay, or dispersion of a dead volume (indicating a void volume).

In addition, the connecting terminal 6 corresponding to the first connecting terminal and the connecting terminal 21 corresponding to the second connecting terminal are provided. Moreover, the pinch valve 7 corresponding to the first opening and closing device and the pinch valve 22 corresponding to the second opening and closing device are provided. The pinch valve 22 causes the target liquid to be collected (blood) to flow to the flow path (the fourth flow path 23 in each of the present embodiments) branched with the connecting terminal 21 from the side adjacent to the collecting source side as the liquid supply side. The pinch valve 7 causes the target liquid to be collected (blood) to flow to another flow path (the second flow path 3 in each of the present embodiments) branched with the connecting terminal 6 away from the side adjacent to the collecting source. This allows continuous flow of the target liquid to be collected (blood) by the pinch valve 22 from the collecting source side. Consequently, the fresh liquid (blood) can flow continuously with no push back of the target liquid to be collected (blood) flowing away from the collecting source side into the collecting source side (i.e., the upstream), and thus the target liquid to be collected (blood) can flow into the flow path branched with the connecting terminal 6 away from the collecting source side as necessary (in a collecting time) and be collected. This allows collection of a fresh liquid (blood) from the collecting source Examples of the flow path in each of the present embodiments include a tube. A tube has a restoring force against external pressure. Accordingly, the first opening and closing device or the second opening and closing device can be formed by the pinch valve 7 or 22 mentioned above. In addition, examples of the first opening and closing device include the pinch valve 7 that closes the flow path formed by a tube by application of external pressure and opens the flow path formed by the tube by releasing the external pressure. The flow path in the present embodiment has a dead volume smaller than that of a valve (opening and closing device) into which the liquid is inserted. Moreover, only replacement of the flow path formed by the tube is required. Accordingly, no replacement of the first opening and closing device is required. Furthermore, the opening and closing device formed by the pinch valve 7 is small in size. Consequently, the device can be installed adjacent to the supply source (collecting source) of the liquid (blood). Moreover, a factor responsible for a distortion of a concentration waveform, such as reduction, delay, or dispersion of a dead volume (indicating a void volume) can be eliminated. As in each of the present embodiments, when the target liquid to be collected is blood of an animal, the pinch valve 7 can be installed adjacent to the animal as the collecting source. In addition, the tube may be formed to have a small diameter (to be thin). Consequently, since the flow path in which the liquid flows becomes thinner, opening and closing of the tube with the pinch valve 7 using the thin tube as the flow path achieves reduction in volume of the flow path and in volume of the liquid to flow.

Moreover, a suppressed flow rate is obtainable by reduction in volume of the flow path and in volume of the liquid (blood) to flow. For instance, when the target liquid to be collected is blood, minimalized reduction in blood loss due to continuous flow of the blood is obtainable.

Moreover, in each of the present embodiments, the pinch valve 7 is so configured as to close one of the two flow paths (the first flow path 2 and the second flow path 3) formed by the tube when opening the other of the flow paths. The construction of the pinch valve 7 to open one path while closing the other path achieves opening and closing of the two flow paths with one pinch valve. This allows reduction in number of components of the first opening and closing device.

Similar to the pinch valve 7 corresponding to the first opening and closing device, the pinch valve 22 corresponds to the second opening and closing device in each of the present embodiments. As is described in Operation and Effect of the pinch valve 7, only replacement of the flow path (i.e., the fourth flow path 23) formed by the tube is required. Accordingly, replacement of the second opening and closing device is not required. The pinch valve 22 can be installed adjacent to the supply source (collecting source) of the liquid (blood). This achieves further reduction in dead volume between the collecting source and the opening and closing device.

In each of the present embodiments, the blood has been described as one example of the target liquid to be collected. Accordingly, the liquid collecting apparatus is an apparatus for performing blood collection, i.e., the blood collecting apparatus 1. Moreover, the liquid collecting method is a method of performing blood collection, i.e., the blood collection method.

With the liquid collecting method according to Embodiment 1, the liquid (blood) is collected using the liquid collecting apparatus (blood collecting apparatus 1 in each of the present embodiments). This allows collection of the liquid by a given volume without measuring a length or an amount of the target liquid to be collected (blood) with a volume measuring device (e.g., an optical measuring device). Moreover, the target liquid to be collected (blood) flows into the flow path (fourth flow path 23) branched with the connecting terminal 21 and flows into the flow path (second flow path 3) branched with the connecting terminal 6, and the liquid (blood) flowing in the flow path (second flow path 3) branched with the connecting terminal 6 is collected at the highest priority. This achieves collection of a fresh liquid (blood) from the collecting source of the liquid (blood) as the supply source.

With the blood collection method including the Steps S1 to S6 in FIGS. 2 and 3, the first drain in the Step S1, the first suction in the Step S2, the second drain in the Step S3, and the second suction and third drain in the Step S4 are performed in turn. Consequently, the target liquid to be collected (blood) flows to the fourth flow path 23 branched with the connecting terminal 21, and flows to the second flow path 3 branched with the connecting terminal 6. Then the liquid (blood) flowing in the second flow path 3 branched with the first connecting terminal 6 is collected at the highest priority. This achieves efficient collection of a fresh liquid (blood).

Moreover, in the present embodiment 1, after the second suction and third drain in the Step S4, the pinch valve 7 opens the first flow path 2 and closes the second flow path 3. The pinch valve 22 opens the fourth flow path 23. Under such a condition, the fluid (the liquid L and the gas G) is pushed together with the target liquid to be collected (blood) drained in the Step S4 until the upstream end of the fluid (the liquid L and the gas G in the present embodiment 1) reaches the connecting terminal 22, whereby the liquid (blood) adjacent to the collecting source flows into the fourth flow path 23 by the Step S6 of pushing back. After the Step S6 of pushing back, the first suction in the Step S2, the second drain in the Step S3, and the second suction and third drain in the Step S4 are repeatedly performed. Such is preferable. This achieves multiple-time collection of a fresh liquid (blood) (multiple-time blood collection) with high efficiency.

The fluid of the present embodiment 1 is composed of the liquid L and the gas G. The part of the flow path adjacent to the suction drain mechanism 5 is filled with the liquid L. Then gas G is inserted in the flow path between the liquid L with which the part of the flow path adjacent to the suction drain mechanism 5 is filled and the target liquid to be collected (blood BL in FIGS. 1 and 3). The suction drain mechanism 5 pushes and pulls the liquid L with which the part of the flow path adjacent to the suction drain mechanism 5 is filled to push and pull the gas G, whereby movement of the target liquid to be collected (blood) is controlled. Filling the flow path with the liquid L different from the target liquid to be collected (blood) and inserting the gas G between the liquid and the target liquid to be collected (blood) allows reduction in volume of gas G compressed or expanded due to push and pull by the suction drain mechanism 5. This achieves movement of the target liquid to be collected (blood) with high accuracy. Moreover, the gas G is inserted between the liquid L with which the part of the flow path adjacent to the suction drain mechanism 5 is filled and the target liquid to be collected (blood). This allows prevention of mixing due to contact of the former liquid L and the latter liquid (target to be collected) (blood). This also allows prevention of dilution of the target liquid to be collected (blood) resulting from the mixing.

EMBODIMENT 2

Figure 4:
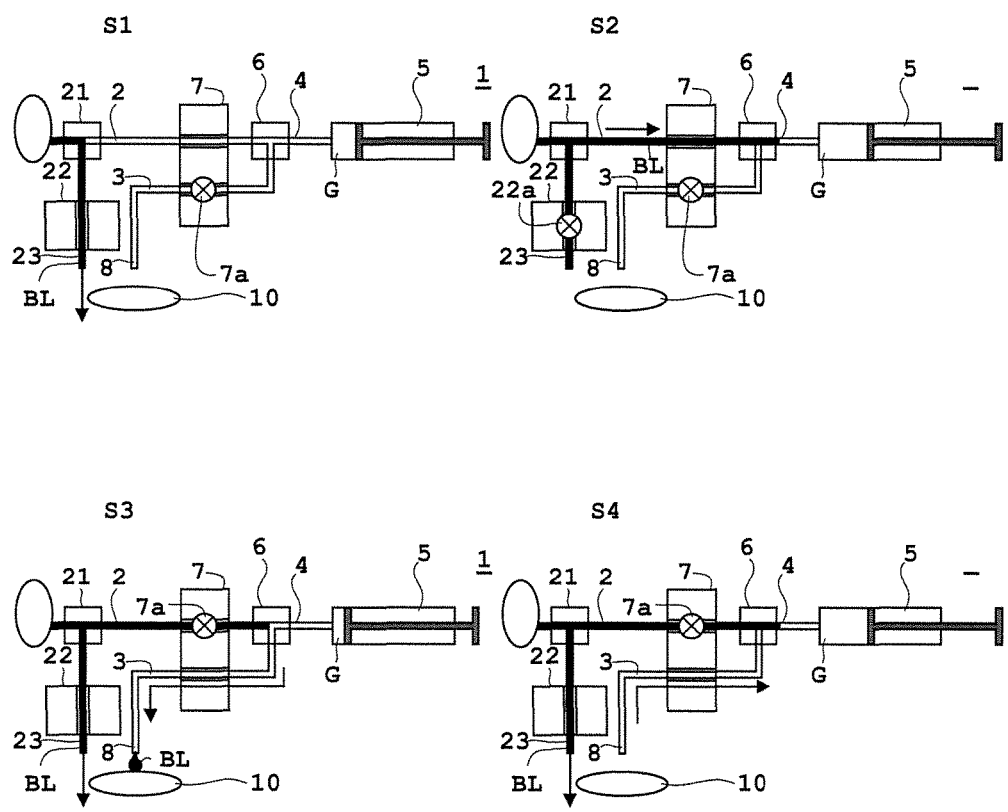
FIG. 4 schematically illustrates a series of blood collecting processes in turn according to Embodiment 2.

The following describes Embodiment 2 of the present invention with reference to drawings. FIG. 4 schematically illustrates a series of blood collecting processes in turn according to Embodiment 2. Parts in common with Embodiment 1 above are denoted by the same numerals, and description thereof is to be omitted.

As illustrated in FIG. 1, a blood collecting apparatus 1 according to the present embodiment 2 has the same construction as the blood collecting apparatus 1 of Embodiment 1. Embodiment 2 differs from Embodiment 1 in that only a gas is adopted as a medium (fluid) to be pushed and pulled. In FIG. 4, the part of the flow path adjacent to the suction drain mechanism 5 rather than the target liquid to be collected (blood) is filled with a gas G, and pushes and pulls the gas G with which the part of the flow path adjacent to the suction drain mechanism is filled. Consequently, movement of the target liquid to be collected (blood) is controlled.

The gas G is not particularly limited. For instance, the gas may be air as in Embodiment 1. Alternatively, the gas may be an inert gas representative of a noble gas such as helium, neon, and argon, or a nitrogen gas that does not react with blood or a heparin solution. The gas G is also indicated in white in FIG. 4.

Since a flow chart of Steps S1 to S6 is same as that of Embodiment 1, the description thereof is to be omitted.

Since the operations and effects of the blood collecting apparatus 1 and the blood collection method according to the present embodiment 2 are same as that of Embodiment 1, the description thereof is to be omitted. In the present embodiment 2, the suction drain mechanism 5 pushes and pulls the gas G as the medium. This allows control of the movement of the target liquid to be collected (blood).

EMBODIMENT 3

Figure 5:
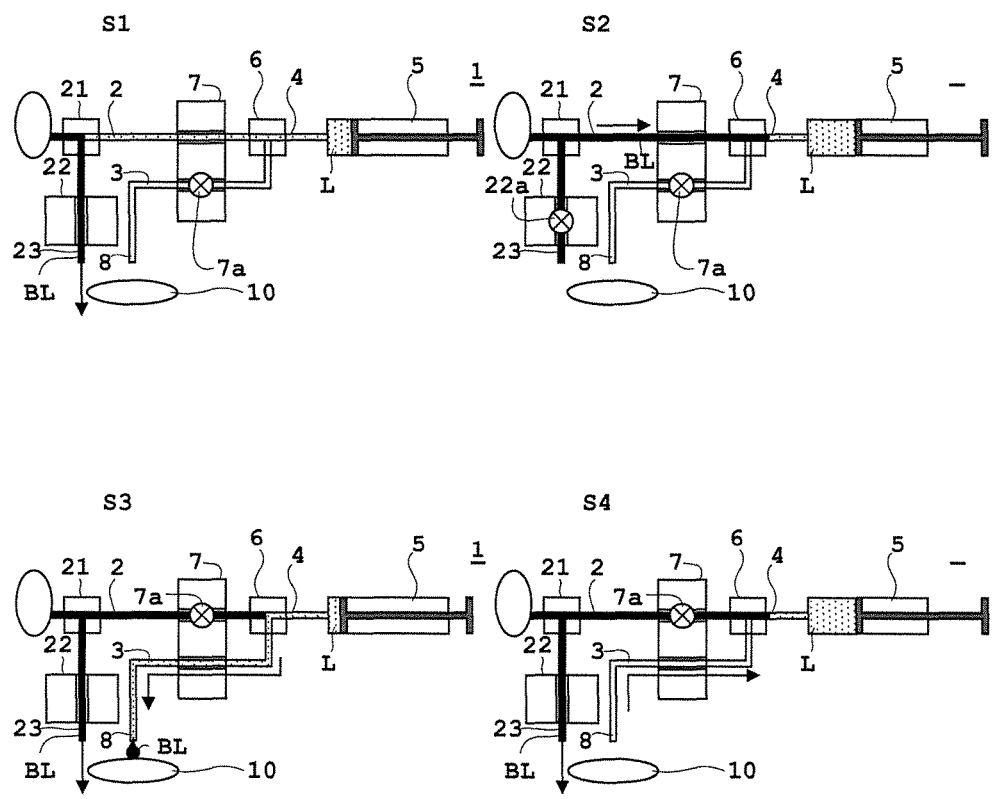
FIG. 5 schematically illustrates a series of blood collecting processes in turn according to Embodiment 3.

The following describes Embodiment 3 of the present invention with reference to drawings. FIG. 5 schematically illustrates a series of blood collecting processes in turn according to Embodiment 3. Parts in common with Embodiments 1 and 2 above are denoted by the same numerals, and description thereof is to be omitted.

As illustrated in FIG. 1, a blood collecting apparatus 1 according to the present embodiment 3 has the same construction as the blood collecting apparatus 1 of Embodiments 1 and 2. Embodiment 3 differs from Embodiments 1 and 2 in that only a liquid is adopted as a medium (fluid) to be pushed and pulled. In FIG. 5, the part of the flow path adjacent to the suction drain mechanism 5 rather than the target liquid to be collected (blood) is filled with a liquid L, and pushes and pulls the liquid L with which the part of the flow path adjacent to the suction drain mechanism 5 is filled. Consequently, movement of the target liquid to be collected (blood) is controlled.

For the liquid adopted as the medium (fluid) to be pushed and pulled, the liquid contacts the target liquid to be collected (blood). Accordingly, the target liquid to be collected (blood) is not completely pushed out from the dropping port for preventing the liquid as the medium (fluid) from dropping together with the target liquid to be collected (blood).

The liquid L is not particularly limited, As in Embodiment 1, the liquid L may be a heparin solution, water, and a mineral oil. The liquid L is also indicated by dotted hatching in FIG. 5.

Since a flow chart of Steps S1 to S6 in Embodiment 3 is same as those in Embodiments 1 and 2, the description is to be omitted.

Since the operations and effects of the blood collecting apparatus 1 and the blood collection method according to the present embodiment 3 are same as those of Embodiments 1 and 2, the description thereof is to be omitted. In the present embodiment 3, the suction drain mechanism 5 pushes and pulls the liquid L as the medium. This allows control of the movement of the target liquid to be collected (blood).

Experimental Result

Figure 6:
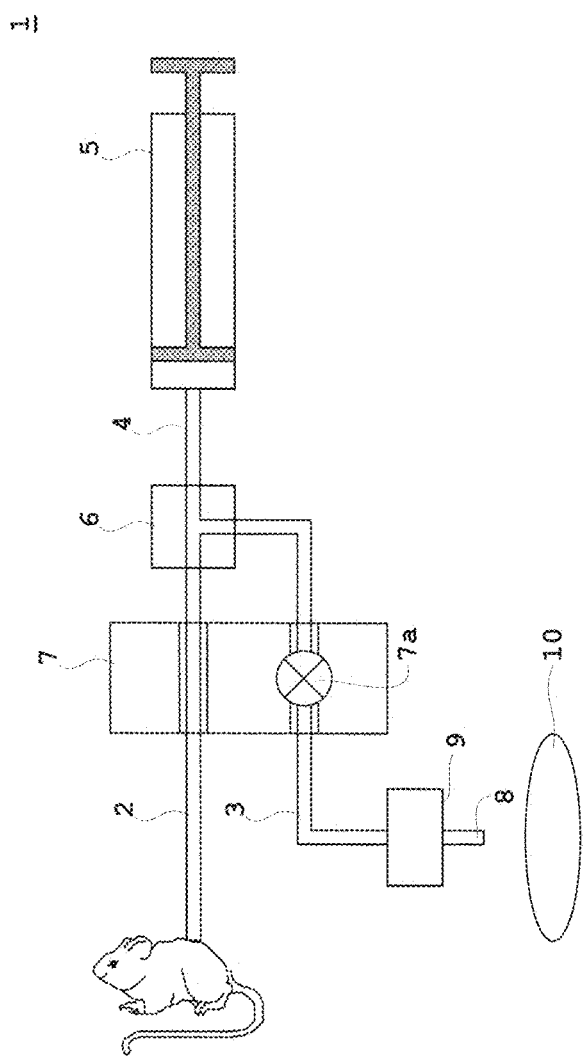
FIG. 6 schematically illustrates a blood collecting apparatus having no fourth flow path.
Figure 7:
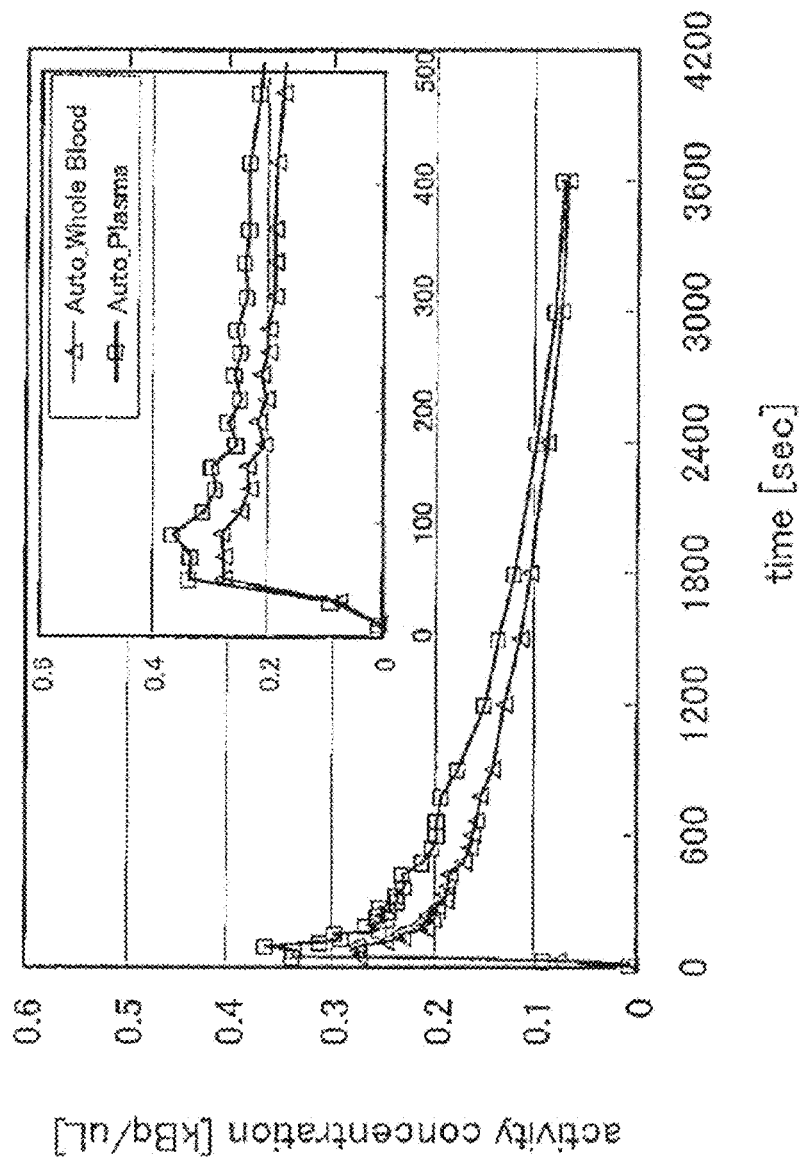
FIG. 7 illustrates one example of an experimental result from the blood collecting apparatus of FIG. 6.
Figure 8:
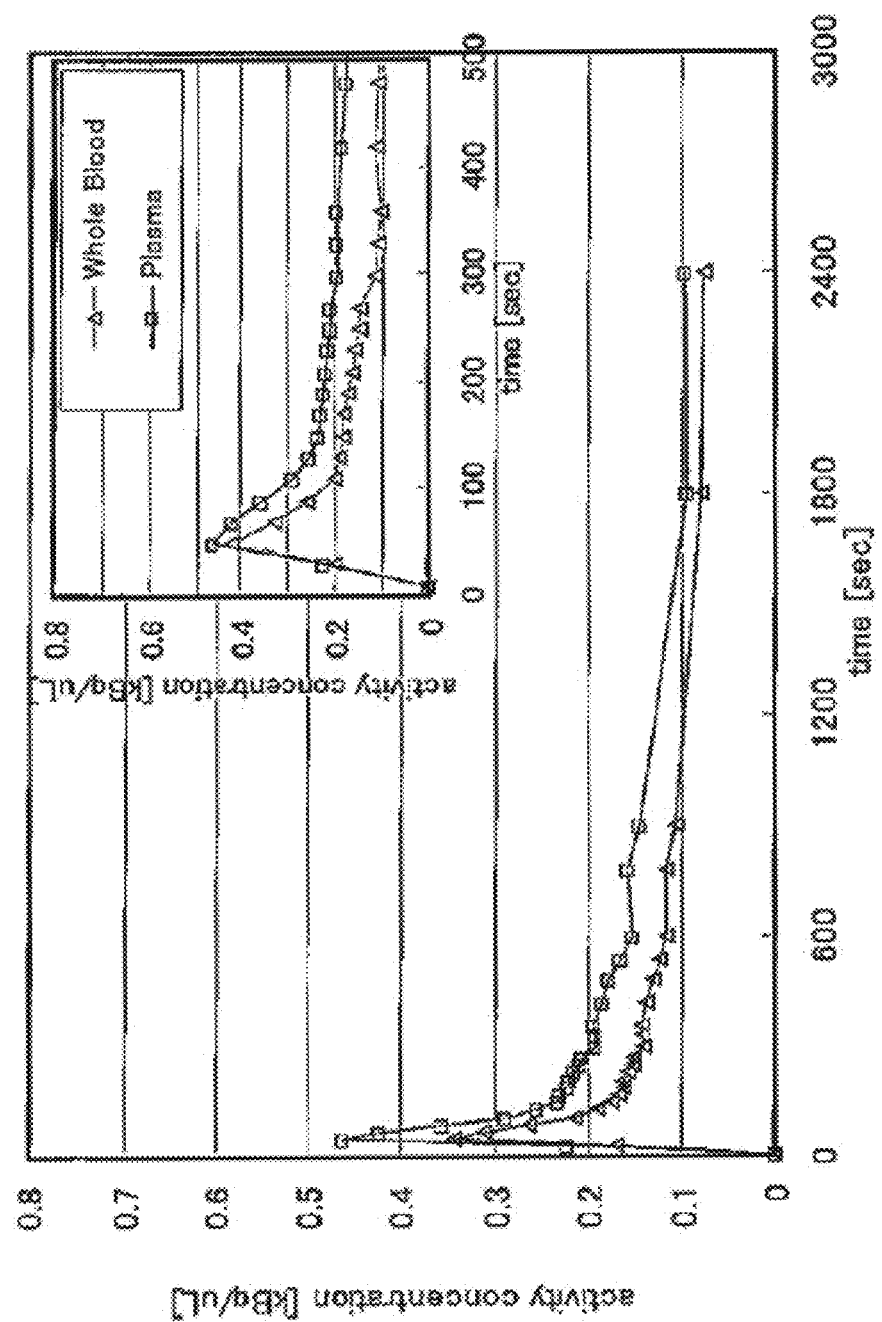
FIG. 8 illustrates one example of an experimental result from the blood collecting apparatus of FIG. 1.
Figure 9:
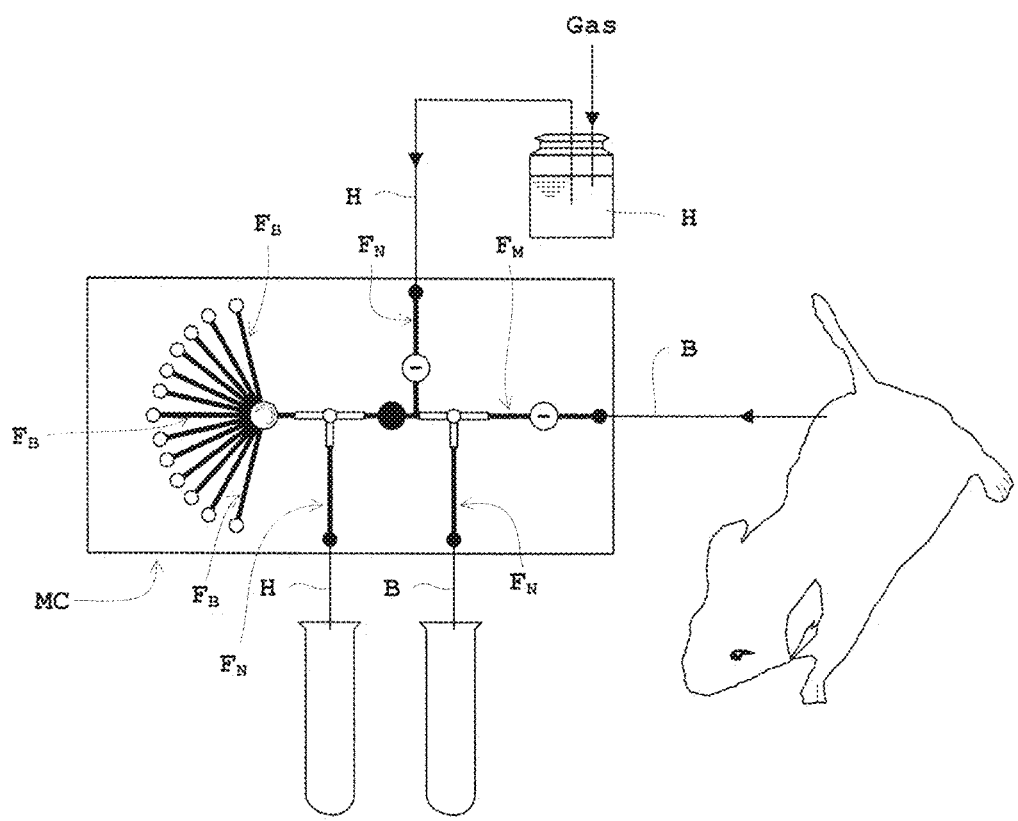
FIG. 9 is a plan view illustrating a conventional microchip entirely in a mode with a microfluidic device.
Figure 10:
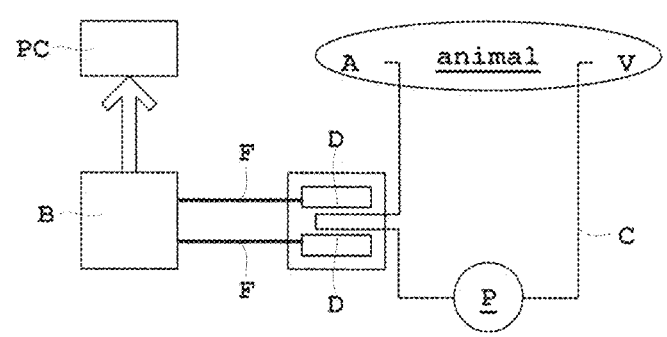
FIG. 10 schematically illustrates a conventional blood collecting apparatus in a mode of flowing blood back into vein from one end of a catheter inserted into arteria.

The following describes an experimental result (FIG. 7 and FIG. 8). The experimental result is obtained by comparison between the blood collecting apparatus in FIG. 1 according to each of the present embodiments and a blood collecting apparatus in FIG. 6 having no fourth flow path and performing minimized discard of blood. FIG. 6 schematically illustrates a blood collecting apparatus having no fourth flow path. FIG. 7 illustrates one example of an experimental result from the blood collecting apparatus of FIG. 6. FIG. 8 illustrates one example of an experimental result from the blood collecting apparatus of FIG. 1. Parts in common with FIG. 1 are denoted by the same numerals, and description thereof is to be omitted.

In FIGS. 7 and 8, a horizontal axis indicates a time axis (denoted by "time [see]"), and a longitudinal axis indicates a radioactive concentration in blood (denoted by "activity concentration [kBq/µL]"). Measurement is performed to whole blood (denoted by "Whole Blood") and plasma (denoted by "Plasma"). A graph in an inside box is an enlarged time axis in an outside box.

FIG. 6 differs from FIG. 1 in the feature that the connecting terminal 21, the pinch valve 22, and the fourth flow path 23 are not provided, and thus minimized blood discard is performed. Moreover, the second flow path 3 and the dropping port 8 in FIG. 1 are only used for collecting. In contrast to this, the second flow path 3 and the dropping port 8 in FIG. 6 have both functions of collecting blood and ejecting and discarding unnecessary blood.

Consequently, upon ejection and discard of the unnecessary blood in FIG. 6, a dropping port moving mechanism 9 moving the dropping port 8 is provided for not locating the container 10 immediately below the dropping port 8. The dropping port moving mechanism 9 has a function of moving the dropping port 8 to change a dropping position of the target blood as separated. The dropping port moving mechanism 9 adopts an electric slider with a stepping motor for changing a position of the dropping port 8 forward/backward and rightward/leftward (horizontally).

In FIG. 6, as is described in Patent Literature 2, blood is pushed back into the body of the animal. Such a process is performed for every completion of blood collection in order to achieve reduction in blood loss. When an interval of the blood collection is short, such as 10 seconds or 20 seconds, a next blood collection timing for drawing blood comes immediately after the blood is pushed back. Consequently, a radioactive concentration in blood to have a peak after collection of the pushed back blood is not measurable accurately. That is, the peak becomes broad as illustrated in the graph in the inside box of FIG. 7.

In contrast to this, for FIG. 1, constant collection of fresh blood is obtainable as mentioned above. Accordingly, an abrupt peak of a radioactive concentration in blood is obtainable as illustrated in the graph in the inside box of FIG. 8.

The experimental result in FIG. 8 has been conducted for a long time of period, i.e., for 40 minutes. Consequently, continuous flow of blood from the fourth flow path 23 may cause the animal to drop dead. Accordingly, on and after five minutes in which an interval of blood collection becomes longer, the pinch valve 22 is closed during a standby time to next blood collection to stop flowing of blood from the fourth flow path 23, whereby achieving reduction in blood loss. Then the pinch valve 22 is opened just before the next blood collection to open the fourth flow path 23, whereby the pushed back blood is ejected and fresh blood is collected.

The present invention is not limited to the embodiments mentioned above, but may be modified as under.

(1) In the liquid collecting apparatus (the blood collecting apparatus 1 in each of the present embodiments) and the liquid collecting method, blood has been described as one example of the target liquid to be collected. However, the blood is not limitative for the target liquid to be collected. For instance, physiological fluid other than blood (e.g., lymph or protein-containing liquid), a fluorescence agent-containing liquid, or a mixed liquid for an analyzer is adoptable.

(2) The first connecting terminal in each of the present embodiments mentioned above branches the first flow path 2 into the two flow paths, i.e., the second flow path 3 and the fourth flow path 4. That is, the number of the branched flow path is two. However, the number may be three or more as long as the number is the plural. That is, the first connecting terminal may branch the flow path into three or more flow paths. For instance, the first flow path 2 in FIG. 1 may be branched into two or more second flow paths 3 and the same number of dropping ports may be provided. Alternatively, the two or more second flow paths 3 may be joined in midstream. Similarly, the first flow path 2 in FIG. 1 may be branched into two or more third flow paths 4 and the same number of suction drain device (suction drain mechanism) may be provided. Alternatively, the two or more third flow paths 4 may be joined in midstream. In addition, another flow path for ejection only may be provided other than the fourth flow path 23. The first connecting terminal may branch the flow path into three or more. Similarly, the second connecting terminal branches the flow path into the number of two in each of the present embodiments. Alternatively, the number may be three or more as long as the number is plural. The second connecting terminal may branch the flow path into three or more. For instance, the fourth flow path in FIG. 1 may be branched into two or more, or the branched flow paths may be joined in midstream.

(3) In each of the present embodiments, the flow path is a tube. Alternatively, the flow path may be a groove on a substrate. In this case, the first and second opening and closing devices preferably open and close the groove using a valve, other than a pinch valve, that passes liquid inside.

(4) In the present embodiments, the first and second opening and closing devices are each a pinch valve. Alternatively, as is described in the modification (3), the opening and closing devices may each be a valve, other than a pinch valve, that passing liquid inside.

(5) In the present embodiments, only a part of the flow path pinched with the pinch valve is a SILASCON tube, and the other part is formed by the first flow path, the second flow path, and the fourth flow path. However, SILASCON is not limitative. For instance, each of the flow paths may be formed by a soft tube made of rubber having a restoring force, such as silicone, Tygon, and polyurethane. Alternatively, only the pinched part is not necessarily made of other materials. That is, the first flow path, the second flow path, and the fourth flow path, or the first to fourth flow paths entirely may be made of the same material.

(6) The pinch valve 7 in each of the present embodiments opens one of the two flow paths formed by a tube (the first flow path 2 and the second flow path 3 in the present embodiments) while closing the other. Alternatively, similar to the pinch valve 22, the pinch valve 7 may open and close one flow path (the fourth flow path 23 in the present embodiments) formed by a tube. For instance, for FIG. 1, a pinch valve for only the first flow path that opens and closes only the first flow path 2, and a pinch valve for the second flow path only that opens and closes only the second flow path 3 may be each provided.

(7) No dropping port moving device (dropping port moving mechanism) is provided in each of the present embodiments. Alternatively, the dropping port moving mechanism 9 as in FIG. 6 may be provided. With a plurality of accommodating portions (grooves) to which dropping is performed, the dropping port moving mechanism 9 moves the dropping port 8 in accordance with positions of the accommodating portions, allowing dropping of the liquid into the accommodating portions individually. When the container to which the dropping is performed is moved, the liquid collecting apparatus (the blood collecting apparatus 1 in the present embodiments) requires no dropping port moving device. Of source, the liquid collecting apparatus (the blood collecting apparatus 1 in the present embodiments) may include the dropping port moving device for relatively moving the dropping port and the containers to which the dropping is performed (or moving one while fixing the other, or moving together relatively). Moreover, a movement of the dropping port moving device is not limited to parallel movement. For instance, rotating movement may be adopted.

(8) In each of the present embodiments, the liquid flowing in the fourth flow path is discarded. However, when not a so fresh liquid is required and thus the liquid is secondarily used, it is not always needed to discard the liquid flowing in the fourth flow path. If the liquid flowing in the flow path branched with the first connecting terminal (the connecting terminal 6 in the present embodiments) is collected at the highest priority, also the target liquid to be collected flowing in the flow path branched with the second connecting terminal (the connecting terminal 21 in the present embodiments) may be collected and reused.

REFERENCE SIGN LIST

1 . . . blood collecting apparatus
2 . . . first flow path
3 . . . second flow path
4 . . . third flow path
5 . . . suction drain mechanism
6, 21 . . . connecting terminal
7, 22 . . . pinch valve
8 . . . dropping port
BL . . . blood
L . . . liquid
G . . . gas

The invention claimed is:

1. A liquid collecting apparatus for collecting a target liquid to be collected as separated in a time series, the liquid collecting apparatus comprising:
a flow path including a main path including first and third path portions, the first portion connected to a collecting source;
a suction drain device connected to the third path portion and operable to selectively apply a positive or negative pressure against the target liquid to be collected;
a first connecting terminal provided on the third path portion, through which a second path portion is branched from the third path portion;
a first opening and closing device provided on the main path and between the first and third path portions, the first opening and closing device being operable to selectively open and close the main path and the second path portion;
a second connecting terminal provided on the first path portion, through which a fourth path portion is branched from the first path portion;
a second opening and closing device operable to selectively open and close the fourth path portion; and
a dropping port connected to the second path portion and configured to drop the liquid to be collected as separated,
the flow path being a tube,
the first opening and closing device being a pinch valve configured to close the main path and the second path portion in response to application of an external pressure and to open the main path and the second path portion in response to releasing of the external pressure, and
the pinch valve being configured to open one of the main path and the second path portion while closing another of the main path and the second path portion.

2. The liquid collecting apparatus according to claim 1, wherein
the second opening and closing device is a pinch valve configured to close the fourth path portion by application of another external pressure and opens the fourth path portion by releasing the another external pressure.

3. The liquid collecting apparatus according to claim 1, wherein
the target liquid to be collected is blood, and
the liquid collecting apparatus is an apparatus that performs collection of the blood.

4. A liquid collecting method of collecting a target liquid to be collected as separated in a time series using a liquid collecting apparatus, the liquid collecting apparatus being provided with a flow path including a main path including first and third path portions, the first portion connected to a collecting source, a suction drain device connected to the third path portion and operable to selectively apply a positive or negative pressure against the target liquid to be collected, a first connecting terminal provided on the third path portion, through which a second path portion is branched from the third path portion, a first opening and closing device provided on the main path and between the first and third path portions, the first opening and closing device being operable to selectively open and close the main path and the second path portion, a second connecting terminal provided on the first path portion, through which a fourth path portion is branched from the first path portion, a second opening and closing device operable to selectively open and close the fourth path portion, and a dropping port connected to the second path portion and configured to drop the liquid to be collected as separated, the first opening and closing device being a pinch valve configured to close the main path and the second path portion in response to application of an external pressure and to open the main path and the second path portion in response to releasing of the external pressure, and the pinch valve being configured to open one of the main path and the second path portion while closing another of the main path and the second path portion, the method comprising:
filling a part of the third path portion adjacent to the suction drain device rather than the target liquid to be collected with a fluid composed of at least either a liquid or a gas;
pushing and pulling the fluid, with which the third path portion adjacent to the suction drain device is filled, through control of the suction drain device, the first opening and closing device, and the second opening and closing device, thereby controlling movement of the target liquid to be collected; and
flowing the target liquid to be collected to the fourth path portion branched with the second connecting terminal and flowing the target liquid to be collected to the second path portion branched with the first connecting terminal, thereby collecting the liquid flowing in the second path portion branched with the first connecting terminal at the highest priority.

5. The liquid collecting method according to claim 4, wherein the fluid, with which the part of the third path portion adjacent to the suction drain device is filled, is sucked toward the suction drain device, whereby the target liquid to be collected is sucked, and the fluid with which the part of the third path portion adjacent to the suction drain device is filled is pushed back into the collecting source, whereby the target liquid to be collected is pushed back,
the first opening and closing device is configured to open and close the first path portion that is located upstream of the first connecting terminal, and to open and close the second path portion that is located downstream of the first connecting terminal and upstream of the dropping port, the suction drain device is configured to connect to the third path portion branched with the first connecting terminal, the third path portion being as another path portion different from the second path portion connected to the dropping port, and the second opening and closing device is configured to open and close the fourth path portion as a path portion located upstream of the second connecting terminal branched from the first path portion with the second connecting terminal, the liquid collecting method further comprises:

a first drain step, a first suction step, a second drain step, and a second suction and third drain step, in the first drain step, under a condition in which the first opening and closing device opens the first path portion and closes the second path portion and the second opening and closing device opens the fourth path portion, pushing and pulling the fluid with the suction drain device until an upstream end of the fluid reaches the second connecting terminal, thereby flowing the target liquid to be collected to the fourth path portion, in the first suction step after the first drain step, under a condition in which the first opening and closing device opens the first path portion and closes the second path portion and the second opening and closing device closes the fourth path portion, sucking the fluid with the suction drain device until a boundary between the upstream end of the fluid and the target liquid to be collected is located adjacent to the suction drain device rather than the first connecting terminal, in the second drain step after the first suction step, under such a condition in which the first opening and closing device closes the first path portion and opens the second path portion and the second opening and closing device opens the fourth path portion, pushing the fluid with the suction drain device back together with the target liquid to be collected sucked in the first suction step, then stopping the fluid at the dropping port via the second path portion, and ejecting and collecting the target liquid to be collected from the dropping port while the liquid adjacent to the collecting source is flown to the fourth path portion, and in the second suction and third drain step after the second drain step, under a condition in which the first opening and closing device closes the first path portion and opens the second path portion and the second opening and closing device opens the fourth path portion, sucking the fluid with the suction drain device until the upstream end of the fluid is located adjacent to the suction drain device rather than the first connecting terminal, thereby flowing the liquid adjacent to the collecting source to the fourth path portion while the target liquid to be collected is sucked.

6. The liquid collecting method according to claim 5, wherein the method further comprises a pushing back step after the second suction and third drain step, in the pushing back step, under a condition in which the first opening and closing device opens the first path portion and closes the second path portion and the second opening and closing device opens the fourth path portion, pushing the fluid together with the target liquid to be collected sucked in the second suction and third drain step until the upstream end of the fluid is located to the second connecting terminal, thereby flowing the liquid adjacent to the collecting source to the fourth path portion, and after the pushing back step, repeatedly performing the first suction step, the second drain step, and the second suction and third drain step.

7. The liquid collecting method according to claim 4, wherein the fluid is composed of a liquid and a gas, the part of the third path portion adjacent to the suction drain device is filled with the liquid, the gas is inserted into at least a portion of the third path portion between the liquid with which the part of the third path portion adjacent to the suction drain device is filled and the target liquid to be collected, and the suction drain device pushes and pulls the liquid with which the part of the third path portion adjacent to the suction drain device is filled, thereby controlling movement of the target liquid to be collected.

8. The liquid collecting method according to claim 4, wherein the fluid is composed of a gas, the part of the third path portion adjacent to the suction drain device rather than the target liquid to be collected is filled with the gas, and the suction drain device pushes and pulls the gas with which the part of the third path portion adjacent to the suction drain device is filled, thereby controlling movement of the target liquid to be collected.

9. The liquid collecting method according to claim 4, wherein the fluid is composed of a liquid, the part of the third path portion adjacent to the suction drain device rather than the target liquid to be collected is filled with the liquid, and the suction drain device pushes and pulls the liquid with which the part of the third path portion adjacent to the suction drain device is filled, thereby controlling movement of the target liquid to be collected.

10. The liquid collecting method according to claim 4, wherein the target liquid to be collected is blood, and the liquid collecting method is a method of performing collection of the blood.

\* \* \* \* \*